(12) United States Patent
Chang

(10) Patent No.: US 10,130,159 B2
(45) Date of Patent: Nov. 20, 2018

(54) AUTOMATIC SKIN CARE DEVICE AND METHOD

(71) Applicant: Shenzhen Airdrawing Technology Service Co., Ltd, Shenzhen (CN)

(72) Inventor: Jen-Tsorng Chang, New Taipei (TW)

(73) Assignee: Shenzhen Airdrawing Technology Service Co., Ltd, Shenzhen (CN)

( * ) Notice: Subject to any disclaimer, the term of this patent is extended or adjusted under 35 U.S.C. 154(b) by 500 days.

(21) Appl. No.: 14/755,305

(22) Filed: Jun. 30, 2015

(65) Prior Publication Data

US 2016/0213126 A1 Jul. 28, 2016

(30) Foreign Application Priority Data

Jan. 28, 2015 (CN) .......................... 2015 1 0041404

(51) Int. Cl.
*A61B 5/00* (2006.01)
*A45D 44/00* (2006.01)

(52) U.S. Cl.
CPC ............ *A45D 44/00* (2013.01); *A61B 5/0013* (2013.01); *A61B 5/0022* (2013.01); *A61B 5/0077* (2013.01); *A61B 5/441* (2013.01); *A61B 5/742* (2013.01); *A61B 5/7405* (2013.01); *A45D 2044/007* (2013.01)

(58) Field of Classification Search
CPC ..... A61B 5/0077; A61B 5/0013; A61B 5/441; A45D 2044/007
See application file for complete search history.

(56) References Cited

U.S. PATENT DOCUMENTS

| | | | | |
|---|---|---|---|---|
| 2003/0179929 | A1* | 9/2003 | Zhang ................. | A61B 5/0059 382/181 |
| 2006/0142662 | A1* | 6/2006 | Van Beek ............ | A61B 5/0059 600/476 |
| 2014/0171759 | A1* | 6/2014 | White ................. | A61B 5/6835 600/306 |
| 2014/0257145 | A1* | 9/2014 | Emery ................ | A61B 8/4209 601/2 |

\* cited by examiner

*Primary Examiner* — Christian Jang
(74) *Attorney, Agent, or Firm* — ScienBiziP, P.C.

(57) ABSTRACT

A method provided for automatic skin care applied in an automatic skin care device capable of communicating with a cloud sever includes the following steps. An image of a skin of the user is captured and converted into a medical image. The medical image is transmitted to the cloud server, allowing an authorized user of the cloud server to analyze the medical image to determine a state of the skin of the user and determine a skin care suggestion corresponding to the determined state of the skin. The determined state of the skin and the determined skin care suggestion is obtained. The skin is cleaned and/or maintained according to the determined skin care suggestion.

16 Claims, 3 Drawing Sheets

AUTOMATIC SKIN CARE DEVICE AND METHOD

FIELD

The subject matter herein generally relates to an automatic skin care device and an automatic skin care method.

BACKGROUND

Various treatments for human skin are proposed for delaying, minimizing or even eliminating skin hyperpigmentation (such as age spots and freckles), wrinkling and other chronic changes typically associated with skin aging or environmental damage. Skin care devices are needed to provide such kind of treatment.

BRIEF DESCRIPTION OF THE DRAWINGS

Implementations of the present technology will now be described, by way of example only, with reference to the attached figures.

DETAILED DESCRIPTION

Figure 1:
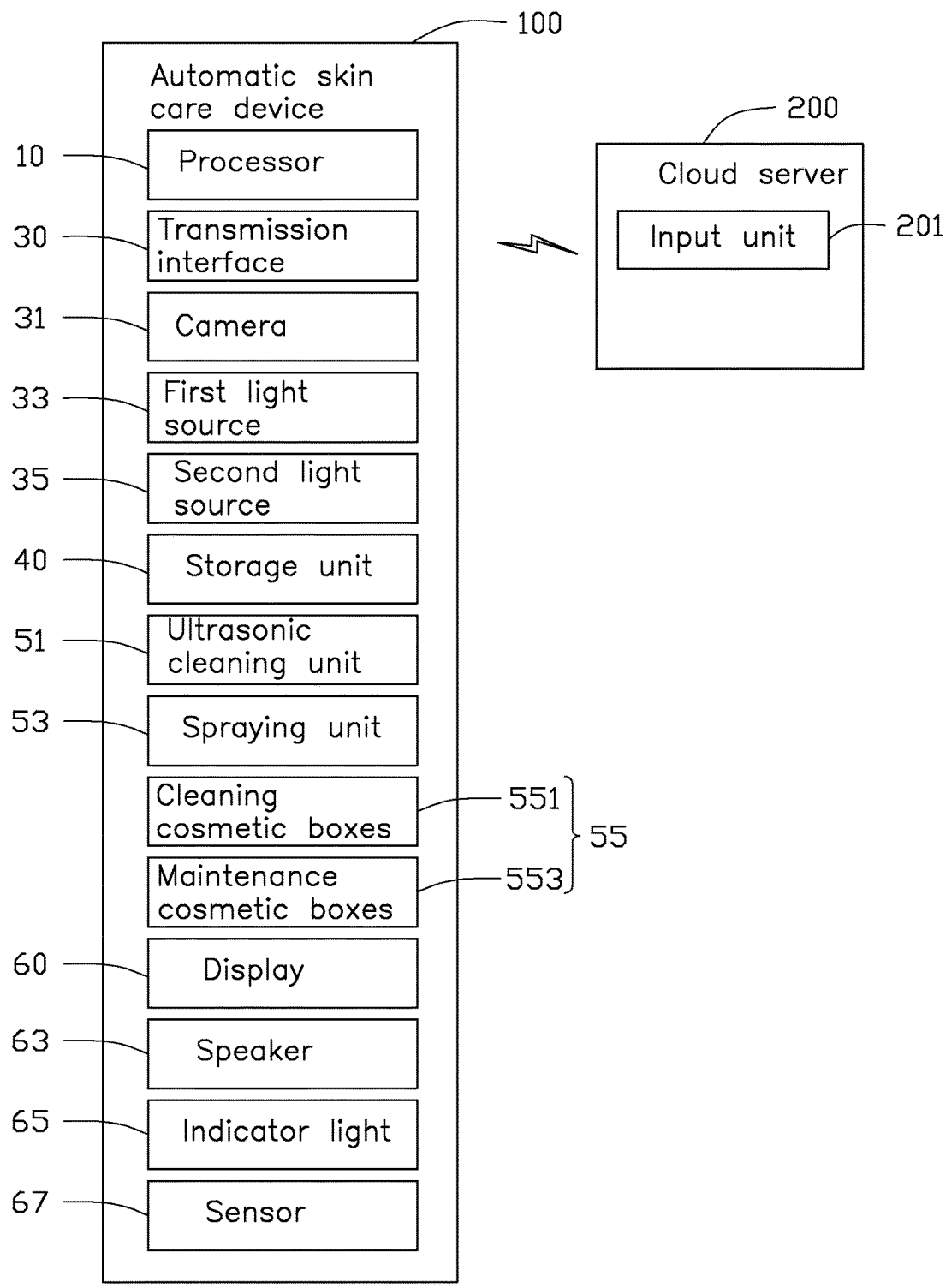
FIG. 1 is a block diagram of an embodiment of an automatic skin care device.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be made to function without these specific details. In other instances, methods, procedures, and components have not been described in detail so as not to obscure the feature being described. Also, the description is not to be considered as limiting the scope of the embodiments described herein. The drawings are not necessarily to scale and the proportions of certain parts have been exaggerated to better illustrate details and features of the present disclosure.

The term "comprising," means "including, but not necessarily limited to" and specifically indicates open-ended inclusion or membership in a combination, group, series, or the like.

FIG. 1 illustrates an embodiment of an automatic skin care device 100 including a processor 10, a transmission interface 20, a camera 31, a first light source 33, a second light source 35, a storage unit 40, an ultrasonic cleaning unit 51, a spraying unit 53, and a number of cosmetic boxes 55. The device 100 is capable of communicating with a cloud server 200.

Figure 2:
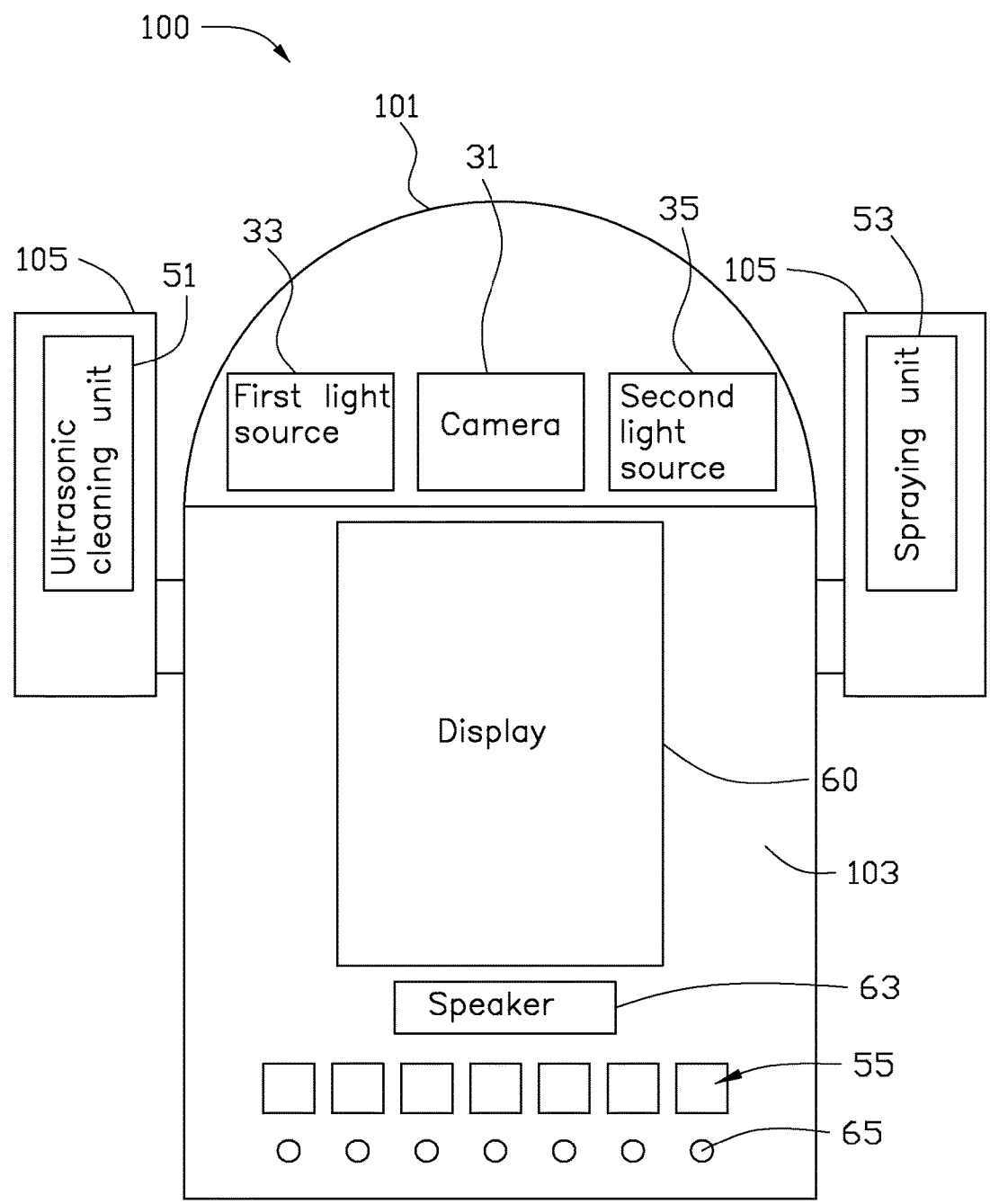
FIG. 2 is a perspective view of the automatic skin care device of FIG. 1.

FIG. 2 illustrates that in at least one embodiment, the device 100 is a robot including a head 101, a body 103 connected to the head 101, and two arms 105 connected to two opposite sides of the body 103. The processor 10, the transmission interface 20, and the storage unit 40 can be mounted on the head 101 or inside the body 103. The camera 31, the first light source 33, and the second light source 35 are mounted on the head 101. The first light source 33 and the second light source 35 are located at two sides of the camera 31. The ultrasonic cleaning unit 51 and the spraying unit 53 are mounted on one arm 105 or on the two arms 105 respectively. The cosmetic boxes 55 are mounted on a front surface of the body 103 to receive different cosmetics. In another embodiment, the configuration of the device 100 can be varied. The locations of the processor 10, the transmission interface 20, the camera 31, the first light source 33, the second light source 35, the storage unit 40, the ultrasonic cleaning unit 51, the spraying unit 53, and the cosmetic boxes 55 can be varied.

The first light source 33 emits a first polarized light towards a user. The second light source 35 emits a second polarized light towards the user. A polarization direction of the first polarized light is different from a polarization direction of the second polarized light. In at least one embodiment, the camera 31 includes an image sensor (not shown) such as a charge coupled device (CCD) or a complementary metal-oxide semiconductor (CMOS). The polarization direction of the first polarized light is parallel to an imaging plane of the image sensor of the camera 31. The polarization direction of the second polarized light is perpendicular to the imaging plane of the image sensor of the camera 31.

The camera 31 captures an image of the skin of the user under an irradiation of the first polarized light and the second polarized light. The image can be stored in the storage unit 40. The user can obtain and check the image as necessary.

The processor 10 obtains the captured image from the camera 31, and converts the obtained image into a medical image including physiological information of the skin. The physiological information of the skin may include a density of the red blood cells gathering on a surface of the skin. Such a converting process of the image into a medical image including the density of the red blood cells gathering on the surface of the skin is known in the art, such as the subject matter of Jim O. Doherty et al., "Sub-Epidermal Imaging using Polarized Light Spectroscopy for Assessment of Skin Microcirculation", Skin Technology and Research, 2007, No. 13, pages 472-484, which is herein incorporated by reference.

In at least one embodiment, the device 100 further includes a display 60 electrically connected to the processor 10. The processor 10 further controls the display 60 to display the medical image after converting the image into the medical image.

The processor 10 further transmits the medical image to the cloud server 200 via the transmission interface 20. As such, an authorized user (such as a dermatologist) of the cloud server 200 can analyze the medical image received by the cloud server 200 to determine a state of the skin of the user, and determine a skin care suggestion corresponding to the determined state of the skin. The cloud server 200 includes an input unit 201. The dermatologist can input the determined state of the skin and the determined skin care suggestion to the cloud server 200 via the input unit 201, to allow the cloud server 200 to transmit the determined state of the skin and the determined skin care suggestion to the device 100 via the transmission interface 20. The transmission interface 20 can be a wireless transmission interface or a wired transmission interface.

In another embodiment, the first light source 33 and the second light source 35 can be omitted. In this case, the camera 31 directly captures the image of the user. The processor 10 directly transmits the image to the cloud server 200, allowing the dermatologist to analyze the image received by the cloud server 200 to determine the state of the skin of the user and determine a skin care suggestion corresponding to the determined state of the skin.

In at least one embodiment, the device 100 further includes a speaker 63 electrically connected to the processor 10. The processor 10 controls the speaker 63 to output the determined state of the skin and the determined skin care suggestion when the device 100 receives the determined state of the skin and the determined skin care suggestion transmitted from the cloud server 200. In another embodiment, the speaker 63 can be omitted, and the processor 10 controls the display 60 to display the determined state of the skin and the determined skin care suggestion.

The ultrasonic cleaning unit 51 and the spraying unit 53 are connected to the cosmetic boxes 55 via pipes (not shown). In one embodiment, the cosmetic boxes 55 include a number of cleaning cosmetic boxes 551 and a number of maintenance cosmetic boxes 553. The cleaning cosmetic boxes 551 are connected to the ultrasonic cleaning unit 51, and receive different cleansing cosmetics. The maintenance cosmetic boxes 553 are connected to the spraying unit 53, and receive different maintenance cosmetics.

The processor 10 further identifies keywords (such as maintaining moisture, reducing inflammation, and anti-acne) included in the determined skin care suggestion when the device 100 receives the determined state of the skin and the determined skin care suggestion. The storage unit 40 stores a relationship between different keywords and skin-care formulations. Each skin-care formulation corresponds to one keyword, and can be obtained by mixing the cosmetic in at least one of the cosmetic boxes 55. The processor 10 determines a skin-care formulation corresponding to the identified keywords according to the stored relationship, and generates a control command according to the determined skin-care formulation. The control command is configured to control the ultrasonic cleaning unit 51 and/or the spraying unit 53 to obtain cosmetics from the corresponding cleaning cosmetic boxes 551 and/or the corresponding maintenance cosmetic boxes 553, and to control the ultrasonic cleaning unit 51 and/or the spraying unit 53 to clean and/or maintain the skin of the user via the obtained cosmetics. In detail, the ultrasonic cleaning unit 51 cleans the skin of the user by emitting ultrasound and spraying the obtained cleansing cosmetics on the skin. The spraying unit 53 sprays the obtained maintenance cosmetics to the skin maintaining the skin of the user.

In one embodiment, the device 100 further includes an indicator light 65 and a sensor 67 corresponding to each of the cosmetic boxes 55. Each indicator light 65 is mounted on the body 103, located under the corresponding cosmetic box 55, and is electrically connected to the processor 10. Each sensor 67 is located in the corresponding cosmetic box 55, and is electrically connected to the processor 10.

Each sensor 67 senses a current amount of cosmetics in the corresponding cosmetic box 55. The processor 10 compares the current amount sensed by each sensor 67 with a preset amount. When one sensed current amount is less than the preset amount, the processor 10 controls the indicator light 65 corresponding to the cosmetic box 55 to flash, to remind the user that the current amount of cosmetics in the cosmetic box 55 is not enough. In addition, when the ultrasonic cleaning unit 51 and/or the spraying unit 53 obtains the cosmetics from the corresponding cosmetic boxes 55, the processor 10 controls the indicator light 65 corresponding to the cosmetic box 55 to flash, to remind the user which cosmetics are currently being used. The preset amount is stored in the storage unit 40.

In at least one embodiment, the device 100 further includes two highly reflective mirrors (not shown) mounted on two sides of the display 60. The user can observe his or her skin via the highly reflective mirrors.

Figure 3:
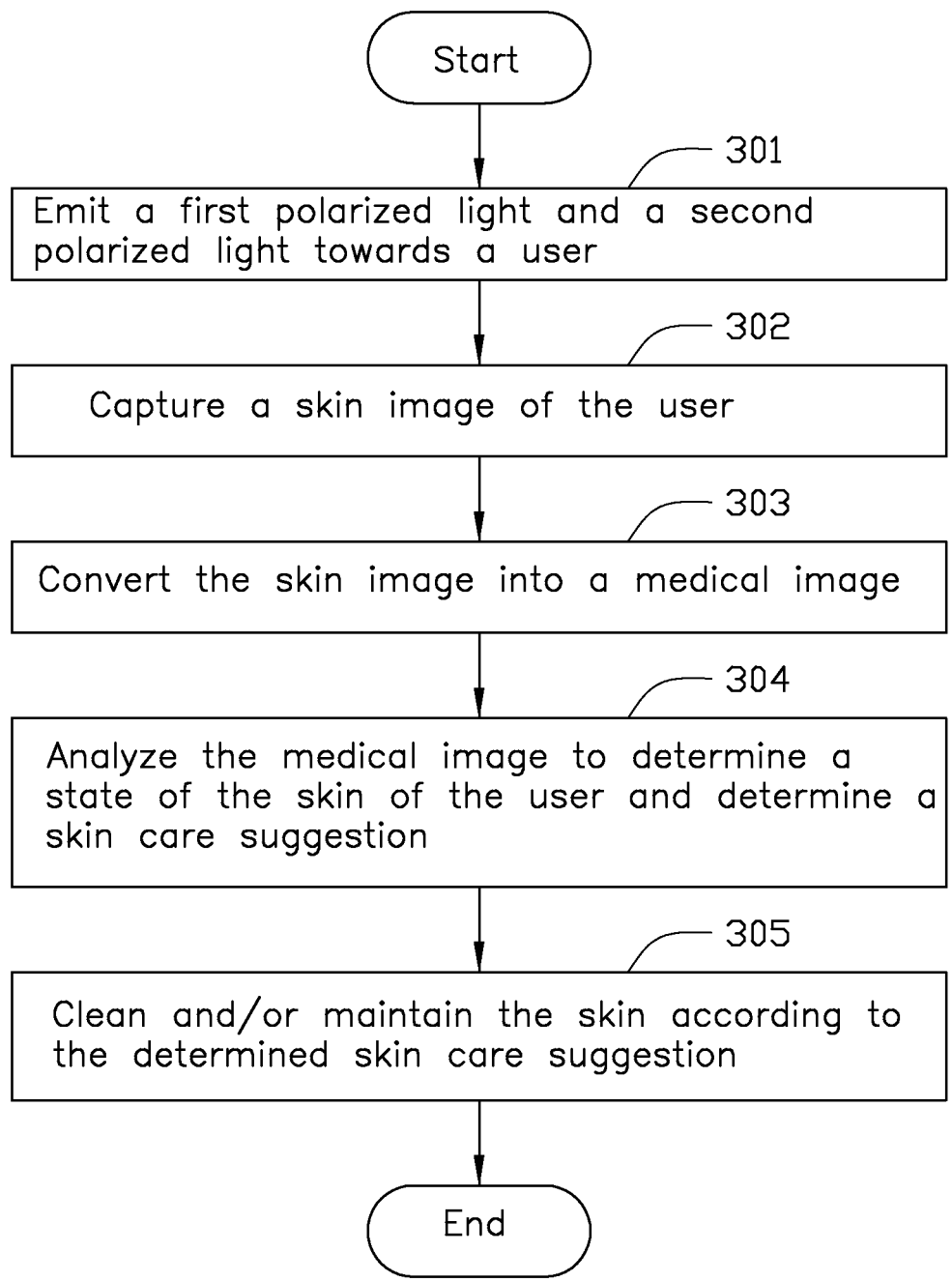
FIG. 3 is a flowchart of an embodiment of an automatic skin care method.

Referring to FIG. 3, a flowchart of an automatic skin care method using the device 100 is presented in accordance with an example embodiment which is being thus illustrated. The example automatic skin care method is provided by way of example, as there are a variety of ways to carry out the method. The automatic skin care method described below can be carried out using the configurations illustrated in FIGS. 1 and 2, for example, and various elements of these figures are referenced in explaining example automatic skin care method. Each block shown in FIG. 3 represents one or more processes, methods or subroutines, carried out in the exemplary automatic skin care method. Additionally, the illustrated order of blocks is by example only and the order of the blocks can change according to the present disclosure. The exemplary automatic skin care method can begin at block 301.

In block 301, a first light source and a second light source respectively emit a first polarized light and a second polarized light towards a user. A polarization direction of the first polarized light is different from a polarization direction of the second polarized light.

In block 302, a camera captures an image of a skin of the user under irradiation of the first polarized light and the second polarized light.

In block 303, a processor obtains the captured image from the camera, and converts the obtained image into a medical image.

In block 304, the processor transmits the medical image to a cloud server via a transmission interface. As such, an authorized user of the cloud server can analyze the medical image received by the cloud server, to determine a state of the skin of the user and determine a skin care suggestion corresponding to the determined state of the skin. Then, the determined state of the skin and the determined skin care suggestion are transmitted to the processor via the transmission interface.

In block 305, the processor identifies keywords included in the corresponding suggestion; a skin-care formulation is determined corresponding to the identified keywords according to a stored relationship between different keywords and skin-care formulations in a storage unit, and a control command is generated according to the determined skin-care formulation. The control command is configured to control an ultrasonic cleaning unit and/or a spraying unit to obtain cosmetics from corresponding cleaning cosmetic boxes and/or corresponding maintenance cosmetic boxes, and to control the ultrasonic cleaning unit and/or the spraying unit to clean and/or maintain the skin via the obtained cosmetics.

It is to be understood, even though information and advantages of the present embodiments have been set forth in the foregoing description, together with details of the structures and functions of the present embodiments, the disclosure is illustrative only; changes may be made in detail, especially in matters of shape, size, and arrangement of parts within the principles of the present embodiments to the full extent indicated by the plain meaning of the terms in which the appended claims are expressed.

What is claimed is:

1. An automatic skin care device capable of communicating with a cloud server, the automatic skin care device comprising:
   a first light source configured to emit a first polarized light;
   a second light source configured to emit a second polarized light, a polarization direction of the first polarized light being different from a polarization direction of the second polarized light;

a camera configured to capture an image of a skin of a user under irradiation of the first polarized light and the second polarized light;

a transmission interface; and a processor configured to obtain the captured image from the camera, convert the obtained image into a medical image, and transmit the medical image via the transmission interface to the cloud server, allowing an authorized user of the cloud server to analyze the medical image to determine a state of the skin of the user and determine a skin care suggestion corresponding to the determined state of the skin;

the processor further configured to obtain the determined state of the skin and the determined skin care suggestion from the cloud server, and clean the skin of the user according to the determined skin care suggestion.

2. The automatic skin care device of claim 1, wherein the polarization direction of the first polarized light is parallel to an imaging plane of an image senor in the camera; the polarization direction of the second polarized light is perpendicular to the imaging plane of the image senor in the camera; the medical image comprises an physiological information of a density of the red blood cells gathering on a surface of the skin.

3. The automatic skin care device of claim 1, further comprising an ultrasonic cleaning unit and a plurality of cleaning cosmetic boxes, wherein the cleaning cosmetic boxes are connected to the ultrasonic cleaning unit and configured to receive different cleansing cosmetics; when automatic skin care device receives the determined state of the skin and the determined skin care suggestion from the cloud server, the processor is configured to control the ultrasonic cleaning unit to obtain cleansing cosmetics from the corresponding cleaning cosmetic boxes, and clean the skin of the user by emitting ultrasound and spraying the obtained cleansing cosmetics towards the skin.

4. The automatic skin care device of claim 3, further comprising a storage unit configured to store a relationship between different keywords and skin-care formulations, wherein the processor is further configured to identify keywords comprised in the determined skin care suggestion, determine a skin-care formulation corresponding to the identified keywords according to the stored relationship, and generate a control command according to the determined skin-care formulation; the control command is configured to control the ultrasonic cleaning unit to obtain cosmetics from the corresponding cleaning cosmetic boxes.

5. The automatic skin care device of claim 4, further comprising a plurality of indicator lights and a plurality of sensors each electrically connected to the processor, wherein each indicator light corresponds to a cleaning cosmetic box; each sensor is located in a cleaning cosmetic box to sense a current amount of cosmetics in the cleaning cosmetic box; the storage unit further stores a preset amount of the cosmetic in each cleaning cosmetic box; the processor is further configured to compare the current amount sensed by each sensor with the preset amount, and control the indicator light corresponding to the cleaning cosmetic box to flash when one sensed current amount is less than the preset amount.

6. The automatic skin care device of claim 5, wherein the processor is further configured to control the indicator light to flash when the ultrasonic cleaning unit obtains the cosmetics from the corresponding cleaning cosmetic box.

7. The automatic skin care device of claim 1, further comprising a speaker electrically connected to the processor, wherein the processor is further configured to control the speaker to output the determined state of the skin and the determined skin care suggestion when the automatic skin care device receives the determined state of the skin and the determined skin care suggestion.

8. The automatic skin care device of claim 1, further comprising a display electrically connected to the processor, wherein the processor is further configured to control the display to display the determined state of the skin and the determined skin care suggestion when the automatic skin care device receives the determined state of the skin and the determined skin care suggestion.

9. The automatic skin care device of claim 8, wherein the processor is further configured to control the display to display the medical image after converting the image into the medical image.

10. An automatic skin care device capable of communicating with a cloud server, the automatic skin care device comprising:

a camera configured to capture an image of a skin of a user;

a transmission interface; and a processor configured to obtain the captured image from the camera, and transmit the image to the cloud server, allowing an authorized user of the cloud server to analyze the image to determine a state of the skin of the user and determine a skin care suggestion corresponding to the determined state of the skin;

the processor further configured to obtain the determined state of the skin and the determined skin care suggestion from the cloud server, and clean the skin of the user according to the determined skin care suggestion;

wherein the automatic skin care device further comprises an ultrasonic cleaning unit and a plurality of cleaning cosmetic boxes, the cleaning cosmetic boxes are connected to the ultrasonic cleaning unit and configured to receive different cleansing cosmetics; when the automatic skin care device receives the determined state of the skin and the determined skin care suggestion from the cloud server, the processor is configured to control the ultrasonic cleaning unit to obtain cleansing cosmetics from the corresponding cleaning cosmetic boxes, and clean the skin of the user by emitting ultrasound and spraying the obtained cleansing cosmetics towards the skin.

11. The automatic skin care device of claim 10, further comprising a storage unit configured to store a relationship between different keywords and skin-care formulations, wherein the processor is further configured to identify keywords comprised in the determined skin care suggestion, determine a skin-care formulation corresponding to the identified keywords according to the stored relationship, and generate a control command according to the determined skin-care formulation; the control command is configured to control the ultrasonic cleaning unit to obtain cosmetics from the corresponding cleaning cosmetic boxes.

12. The automatic skin care device of claim 11, further comprising a plurality of indicator lights and a plurality of sensors each electrically connected to the processor, wherein each indicator light corresponds to a cleaning cosmetic box; each sensor is located in a cleaning cosmetic box to sense a current amount of cosmetics in the cleaning cosmetic box or the maintenance cosmetic box; the storage unit further stores a preset amount of the cosmetic in each cleaning cosmetic box; the processor is further configured to compare the current amount sensed by each sensor with the preset amount, and control the indicator light corresponding to the cleaning cosmetic box to flash when one sensed current amount is less than the preset amount.

13. The automatic skin care device of claim 12, wherein the processor is further configured to control the indicator light to flash when the ultrasonic cleaning unit obtains the cosmetics from the corresponding cleaning cosmetic box.

14. The automatic skin care device of claim 10, further comprising a speaker electrically connected to the processor, wherein the processor is further configured to control the speaker to output the determined state of the skin and the determined skin care suggestion when the automatic skin care device receives the determined state of the skin and the determined skin care suggestion.

15. The automatic skin care device of claim 10, further comprising a display electrically connected to the processor, wherein the processor is further configured to control the display to display the determined state of the skin and the determined skin care suggestion when the automatic skin care device receives the determined state of the skin and the determined skin care suggestion.

16. The automatic skin care device of claim 15, wherein the processor controls the display to display the image.

* * * * *